(12) United States Patent
Grant et al.

(10) Patent No.: US 7,815,586 B2
(45) Date of Patent: Oct. 19, 2010

(54) ADJUSTABLE RESTRAINT FOR THE LOWER LEG AND/OR FOOT

(75) Inventors: William Peter Grant, Virginia Beach, VA (US); Laurence Glenn Rubin, Richmond, VA (US); Steve Cook, Richmond, VA (US); Guy Pupp, Bloomfield Hills, MI (US); David Czenkus, Casco, MI (US); Louis A. Serafin, Jr., Lakeport, MI (US)

(73) Assignee: EZ Concepts Surgical Device Corporation, Marysville, MI (US)

( * ) Notice: Subject to any disclaimer, the term of this patent is extended or adjusted under 35 U.S.C. 154(b) by 349 days.

(21) Appl. No.: 11/885,686

(22) PCT Filed: Feb. 25, 2006

(86) PCT No.: PCT/US2006/006699

§ 371 (c)(1),
(2), (4) Date: Sep. 5, 2007

(87) PCT Pub. No.: WO2006/098864

PCT Pub. Date: Sep. 21, 2006

(65) Prior Publication Data

US 2009/0124947 A1 May 14, 2009

Related U.S. Application Data

(60) Provisional application No. 60/660,139, filed on Mar. 9, 2005.

(51) Int. Cl.
*A61F 5/00* (2006.01)
*A61F 5/04* (2006.01)
*A61F 4/00* (2006.01)
*A61B 17/56* (2006.01)
*A61B 17/00* (2006.01)

(52) U.S. Cl. .............................. 602/23; 602/5; 602/27; 128/846; 128/869; 128/882; 606/53; 606/54; 606/55; 606/56

(58) Field of Classification Search .................... 602/5, 602/16, 23, 26, 27, 31, 60, 61, 62, 65; 128/846, 128/869, 882; 606/53–59
See application file for complete search history.

(56) References Cited

U.S. PATENT DOCUMENTS 2,020,262 A 11/1935 Longfellow .................. 128/84

(Continued)

FOREIGN PATENT DOCUMENTS

WO 2006/098864 9/2006

OTHER PUBLICATIONS

Grant et at., provisional application for U.S. Patent No. 60/660,139, filed Mar. 9, 2005 A.D.

(Continued)

*Primary Examiner*—Patricia M Bianco
*Assistant Examiner*—Brandon Jackson
(74) *Attorney, Agent, or Firm*—Christopher John Rudy (57) ABSTRACT

Adjustable restraint includes a plantar plate surrounded by a peripheral element about which a plurality of supports can be positioned; a support system attachable to that plate or element for providing vertical and horizontal support; and a lower leg securing housing. The housing is attachable to the support system through adjustable fastener(s) such it can be adjusted vertically and secured in position with respect to the plantar plate. A sole portion of the plantar plate may be removable. The support system can include first support(s) and second support(s) attachable to the plate or element, and, through first adjustable fastener(s) and second adjustable fastener(s), respectively, the first adjustable fastener(s) and second adjustable fastener(s) be attachable to the housing.

20 Claims, 7 Drawing Sheets

U.S. PATENT DOCUMENTS

| | | | | |
|---|---|---|---|---|
| 2,079,567 | A | | 5/1937 | Anderson .................... 602/39 |
| 3,651,803 | A | * | 3/1972 | Bimler ........................ 602/16 |
| 4,615,338 | A | | 10/1986 | Ilizarov et al. ............ 128/92 A |
| 5,070,868 | A | | 12/1991 | Hepburn et al. ........... 128/80 R |
| 5,520,627 | A | | 5/1996 | Malewicz .................... 602/26 |
| 5,833,639 | A | | 11/1998 | Nunes et al. ................. 602/23 |
| 6,964,663 | B2 | | 11/2005 | Grant et al. .................. 606/54 |

OTHER PUBLICATIONS

International Search Report and Written Opinion of Jun. 29, 2007 in PCT/US2006/006699.

Medical Shoe Company, VCam Walker, www.medicalshoecompany.com, downloaded Feb. 7, 2006.

Orthopadeics, C&W, The Ilizarov Apparatus, www.cw.bc.ca, downloaded Mar. 31, 2004.

Ultraflexm Brace Designs, www.ultraflexsystems.com, downloaded Mar. 31, 2004.

Communication pursuant to Article 96(2) EPC in European Patent Application No. 04784307.3-2318, Feb. 15, 2007.

Walsh, MacLachlan & Donaldson, response in European Patent Applicaiton No. 04784307.3-2318, Jun. 8, 2007.

Communication pursuant to Article 96(2) EPC in European Patent Application No. 04784307.3-2318, Jul. 27, 2007.

Important Notice with Internaitonal Preliminary Report on Patentability in International Patent Application No. PCT/US2006/006699, Sep. 20, 2007.

USPTO Patent Database Search Results: Ilizarov and (ring or apparatus or device), 1976-Mar. 31, 2004, $1^{st}$ 50 hits, Mar. 31, 2004.

EZ Concepts Surgical Device Corporation, "EZ Frame External Fixator for Limb Salvage, Trauma and Reconstruction of the Foot," brochure ca. 2006.

McKechnie et al. (Eds.), Webster's new Universal Unabridged Dictionary, Deluxe Second Edition, Dorset & Baber, Cleveland, Ohio, 1983, p. 1836.

* cited by examiner

ADJUSTABLE RESTRAINT FOR THE LOWER LEG AND/OR FOOT

This claims priority benefits of U.S. provisional patent application No. 60/660,139 filed on Mar. 9, 2005 A.D. For the US, the same is claimed under Patent Cooperation Treaty and/or Title 35 United States Code, particularly under sections 119(e), 120, 363 and/or 365. Where applicable, as in the US, the complete specification of the '139 application is incorporated herein by reference.

BACKGROUND TO THE INVENTION

I. Field

The present invention concerns an adjustable restraint for the lower leg and/or foot, which is useful in surgically immobilizing bones about the lower tibia, ankle and/or foot, especially through impaling with suitable surgical wire; and its making and use.

II. Art

The Ilizarov ring is a standard device useful in adjusting or setting bones with impaling by a suitable wire. Unfortunately, when restraint of the foot is required, or the ring is employed about the foot, the restraint can become problematic for various reasons, and walking or putting any weight on the restrained foot can be well nigh impossible. However, it is stress on set bones that can speed recovery from a break.

It would be desirable to ameliorate or overcome this.

DISCLOSURE OF THE INVENTION

I. Genesis

It had been decided to restrain the foot undergoing treatment with an Ilizarov ring combined with a rigid boot having a sole that would keep the foot immobilized in relation to the ring. See, U.S. Pat. No. 6,964,663 B2.

Such a basic embodiment, however, useful as it is, may lack adaptability to a wide range of patient configurations and needs.

II. Advances

In address of the above, the present advances can include an adjustable restraint for the lower leg and/or foot comprising:
 a plantar plate surrounded by a peripheral element about which a plurality of supports can be positioned;
 a support system attachable to said plate or element, which can provide vertical and horizontal support in relation to said plate and element; and
 a lower leg securing housing;
wherein the lower leg securing housing is attachable to the support system through at least one adjustable fastener such that the lower leg securing housing can be adjusted vertically with respect to the plantar plate and secured in position therewith. Preferably, the support system includes:
 at least one first support attachable to said plate or element, which has a vertically extending component thereto, and which has upper and lower ends; and
 at least one second support laterally attachable to said plate or element disposed in relation to the at least one first support, which has a horizontally directed component thereto, which has upper and lower ends, and which is attachable about the lower end with a pivoting relationship to said plate or element;

wherein:
 the lower leg securing housing is attachable to the at least one first support through at least one first adjustable fastener; and
 the lower leg securing housing is attachable to the at least one second support through at least one second adjustable fastener.

Advantageously, at least a sole portion of the plantar plate is made to be removable. Other beneficial features can be provided.

The invention is useful in orthopedics and podiatry.

Significantly, by the invention, easy adaptability in a foot or lower leg restraint for surgical application to a wide variety of patient configurations and needs is provided. Moreover, the invention can be provided as a lightweight restraint, which can engender increased mobility and faster, more efficient healing.

Numerous further advantages attend the invention.

The drawings form part of the specification hereof. With respect to the drawings, which are not necessarily drawn to scale, the following is briefly noted.

The invention can be further understood by the present detail as set forth below, which may be read in view of the drawings. Such is to be taken in an illustrative and not necessarily limiting sense.

In general, the advances to the basic embodiment of an Ilizarov ring combined with a rigid boot with a sole to keep the foot immobilized in relation to the ring, include an adjustable restraint for the lower leg and/or foot that embraces a plantar plate surrounded by a peripheral element about which a plurality of supports can be positioned; a support system attachable to the plate and/or element, which can provide vertical and horizontal support in relation to the plate and element; and a lower leg securing housing. The lower leg securing housing is attachable to the support system through at least one adjustable fastener such that the lower leg securing housing can be adjusted vertically with respect to the plantar plate and secured in position therewith. By attachable is meant two or more items can be or are attached directly or indirectly to one another.

The plantar plate is surrounded by a peripheral element, and this plate and peripheral element together may be of one piece or a plurality of pieces. For instance, it may include a monolithic slab of any suitable material such as an appropriate metal, wood, plastic, ceramic, or other composite, in a form of a rectangle or rounded rectangle with rounding at the heel and/or toe, which typically is larger than the footprint of the patient, to serve as a sole and extended welt, as it were. Around the periphery of such, i.e., its peripheral element or so called extended welt, the plurality of supports can be positioned. The slab may be made to include a removable portion, for instance, a part or the whole of the plantar plate, or so called sole, to provide access to the plantar portion of the foot when it is restrained by the device so as to be able to dress or treat the bottom of the foot if necessary or desired. Among supports that are employed about the peripheral element can be vertical post units that secure the well known surgical wires employed in Ilizarov procedures. These vertical posts may be immovable and attached to the peripheral element, even perhaps made monolithically with the element, but preferably, such posts are attachable to the peripheral element at locations selected by the medical practitioner. The locations may be predetermined such as by providing a series of holes about the periphery into which the vertical posts are inserted and then secured as in known Ilizarov rings, or the locations can be more freely determined at the time of surgery by providing a slot or groove, which may have an undercut to form a blind or open upside down T-shape, into which a corresponding part of the vertical posts can be inserted. Securement can be by mechanical fastening such as by nut and bolt tightening, wedging, and so forth, and/or may be by gluing such as with polymethylmethacrylate cement, and so forth and the like.

The support system attachable to the plate and/or element can provide vertical and horizontal support in relation to the plate and element. It may embrace a single subunit attached to or made integrally monolithic with the plate and element, which is stout enough to provide the necessary vertical and horizontal support for the device. However, single subunit embodiments, when made from known materials that can provide the necessary support, most typically suffer from excessive weight, making the final device unwieldy for a patient. Be that as it may, any suitable material may be employed to provide the support system, again to include appropriate metal, wood, plastic, ceramic or other composite. A simple expedient of a vertical post, suitably braced if needed, extending upward, say, from about the heel portion of the plate, perhaps having a series of holes in it to accommodate insertion of pegs, bolts, rivets, or the like, or being of or including a material that can receive fastening screws, accept glue, or the like along its length or part of it, with which to fasten a lower leg securing housing may be provided.

Preferably, the support system includes at least one first support attachable to the plantar plate or peripheral element, which has a vertically extending component, and has upper and lower ends. Stiff, vertically extending rod or rods, desirably of a lightweight material, for example, a carbon fiber reinforced composite, can be employed as part of the first support. To the rod(s) can be attached fastener(s) and/or brace(s), which hold the lower leg securing housing, and which can be slid up or down the rod(s) to a satisfactory height and there secured from vertical movement. Such can embody the at least one first adjustable fastener. Preferably too, the support system includes at least one second support laterally attachable to the plantar plate plate or peripheral element, taken in relation to the at least one first support. The at least one second support has a horizontally directed component, has upper and lower ends, and is attachable about its lower end with a pivoting relationship to the plantar plate or peripheral element. Again, a stiff, vertically extending rod or rods can be employed as part of the second support such as the type employed in the first support. To the rod(s) can be attached fastener(s) and/or brace(s) to directly or indirectly hold the lower leg securing housing. These can be slid up or down the rod(s) to a satisfactory height and there secured from elongate movement. The lower end can be attachable to the plantar plate or peripheral element through a pivoting fastener or fastener component, and the upper end can be attached through a pivoting fastener or fastener component. Such can embody the at least one second adjustable fastener.

The lower leg securing housing is made to externally secure the leg of the patient. It helps restrain the lower extremities of his leg and/or foot in relation to the plantar plate and peripheral element. It may be considered to be a form of a restraining gaiter, typically, however, without an ankle or lower foot portion, but having suitable stiffness and strength to maintain effective restraint of the patient's lower leg. Any suitable material may be employed for the lower leg securing housing, to include an appropriate, thick, stiff leather or cloth or an appropriate plastic, or other composite. An expedient can be provided by cutting the calf portion of a known plastic foot or ankle restraining boot, say, above the ankle, leaving its fasteners such as buckles, clasps, straps, ties, or the like.

Further beneficial features are provided hereby.

With reference to the drawings, adjustable restraint device 100 is useful for surgical restraint of the lower leg and/or foot of a patient. The device 100 may be beneficially employed for treatment of various conditions and diseases.

The device 100 includes plantar plate 10 having base 11, inset-securing slide groove 12, rounded heel walls 13, and removable sole 14. The sole 14 can include tongue 15 for sliding in and out of the groove 12, and rounded forward side walls 16 that can extend substantially in line with the more anterior portions of the sides of the heel wall 13. Peripheral element 20 can be set away from the plate 10, base 11 and/or sole 14, at least in part, and be supported in such a disjunctive configuration by bridges 21. The base 11 with element 20 can be made, for example, by machining a monolithic slab of laminated glass-fiber resin composite plastic, which provides for a more rigid construction than typical metal Ilizarov rings, and the sole 14 can be made, for example, by machining a suitably stiff, monolithic slab of ultra high molecular weight polyethylene (UHMWPE). A preferred, exemplary alternative for the sole 14 is alpha-butylstyrene (ABS) plastic, which, for example, can be machined from a slab, or which may be injection molded. The element 20 can include first receptacle set 22, say, in a form of two posterior holes each surrounded by tab 23, and second receptacle set 24, say, in a form of an extended series of holes, for example, symmetric about central anterior to posterior axis 25, that may be found in recess 26 about a peripheral portion of the element 20. Into the receptacle sets 22, 24 can be positioned two or more supports 30, directly or indirectly.

The supports 30 include the support system that is attachable to the plate 10 or element 20, which provides vertical and horizontal support in relation to the plate 10 and element 20. Vertical support can be provided by first support 31, which, for example, can be a cylindrical carbon composite rod about ¼-inch in diameter, and which has lower end 31L and upper end 31U. Horizontal support can be provided by second support 32 that, in relation to the vertical support 31 can be attached to the plate 10 or element 20 a distance laterally from the first support 31. The horizontal support 32, for example, of the same cylindrical rod material as the vertical support 31, in addition to its horizontal component can have a vertical component. The support 32 also has lower and upper ends, 32L and 32U, respectively, and is attached about the lower end 32L with a pivoting relationship to the plate 10 and element 20. In addition, the support 32 is attached about the upper end 32U with a pivoting relationship with respect to the vertical support 31. Preferably, the carbon rods 31, 32 are braided carbon fiber rods. Post supports 33 are also provided. These are made, for example, of stainless steel metal of a height to extend a suitable distance above the plate 10, say, about from one half to six inches so that, for example, the horizontal support 32 can find an intermediary to the plate 10 and peripheral element 20, and surgical wire (not illustrated in FIGS. 1-19; but see, FIG. 20 feature No. 8) for impaling bone or other tissue for rejuvenation or repair can be securely affixed. The supports 33 can include elongate body 33B, ovoid or side-truncated oval holes 33H, groove-residing shoulder 33S, and threaded lower end 33T. Lower nut 34 may be provided to fasten the support 33 to the plate 10 or element 20. An alternative is to form the lower end of the support 33 to have internal female threads and, in lieu of the nut 34, provide a threaded bolt, say, with a round head and Allen wrench socket. The support 33 can receive surgical wire securing bolt 35, which has wire-receiving hole 35H and nut 35N, which drives the wire against the shoulder 35S and support body 33B when it is tightened onto the threads 35T. Another bolt, say, with a smooth shoulder wider than its threaded tip, can be provided to pivotably hold lower pivot bulb 36, which receives and holds the lower extremity of the lower portion 32L of the rod 32 through hole 36H, onto one of the supports 33, by threading it into receptacle 36R having shoulder 36S and internal threads 36T.

Thus, lower leg securing housing 40, which holds the outside of the lower leg primarily above the ankle and can include brace-securing holes, lower 41L and upper 41U, strap/buckle fastening system 42, and ventilation holes 43, is attachable to the support system 30 through at least one adjustable fastener 50. And so, the housing 40 can be adjusted vertically and secured in position with respect to the plantar plate 10.

Preferably, the support system 30 has more than one adjustable fastener 50. Accordingly, the lower leg securing housing 40 can be attached to the at least one first support 31 through at least one first adjustable fastener 51, which can have body 51B, cut 51C that can be squeezed to clamp down upon the support 31 to stop the fastener 51 from movement in relation to the support 31, brace-mating face 51F, support-receiving slide holes 51H, the top and bottom of which may be chamfered, threaded hole 51T for insertion and threading of a bolt to squeeze the cut 51C together and clamp the support 31 and threaded hole 51TT for insertion and threading of a bolt to secure lower brace 52 to the fastener 51. The brace 52 provides for indirect attachment of the housing 40, and it can include holes 52H for attachment of the fastener 51 as well as attachment together of the housing and operation knob 52K, say, through bolting with threaded bore 52KT, which greatly assists in smooth vertical adjustment of the housing 40. Moreover, the lower leg securing housing 40 can be attached to the at least one second support 32 through at least one second adjustable fastener 53, which, like the first 51, can have body 53B, cut 53C that can be squeezed to clamp down upon the support 31 to stop the fastener 53 from movement in relation to the support 31, brace-mating face 53F, support-receiving slide holes 53H, the top and bottom of which may be chamfered, threaded hole 53T for insertion and threading of a bolt to squeeze the cut 53C together and clamp the support 31, and threaded hole 53TT for insertion and threading of a bolt to secure upper brace 54 to the fastener 53. The brace 54 provides for indirect attachment of the housing 40 also, and it can include holes 54H for attachment of the housing 40 and the fastener 53. Beneficially, as part of or an adjunct to the second adjustable fastener 53, upper pivoting slide body 55 is also provided, which can be made in two mirror image halves 55A and 55B, and which can include threaded, smooth shoulder-containing pivot hole 55P for pivotal attachment to the fastener 53 through a long clamping bolt, and slide hole 55S through which the second support 32 can slide as well. The body 55 is tightened by the clamping bolt when the support 32 is in position to provide the appropriate height of the housing 40 from the plate 10. The fasteners 51, 53, can be made, for example, by machining aluminum metal, and the braces 52, 54 can be made, for example, by machining ABS plastic. The knob 52K can be made by machining ABS plastic.

See, FIGS. 1-19. See also, FIG. 20, a key to which is set forth below (comparisons made to feature numerals above).

Figure 1:
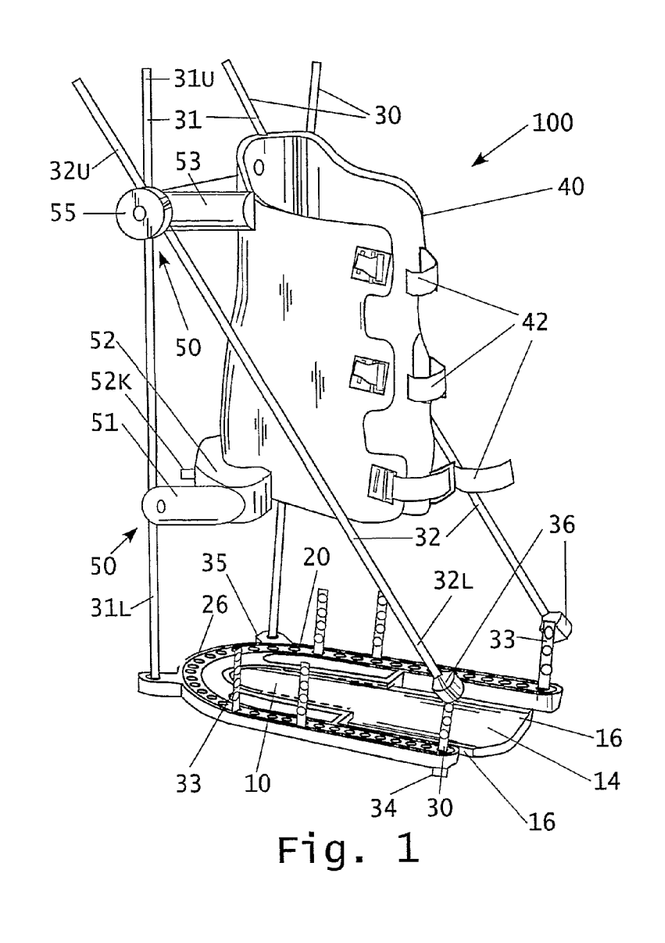
FIG. 1 is a side perspective view of an adjustable restraint device for the lower leg and/or foot of the invention.
Figure 2:
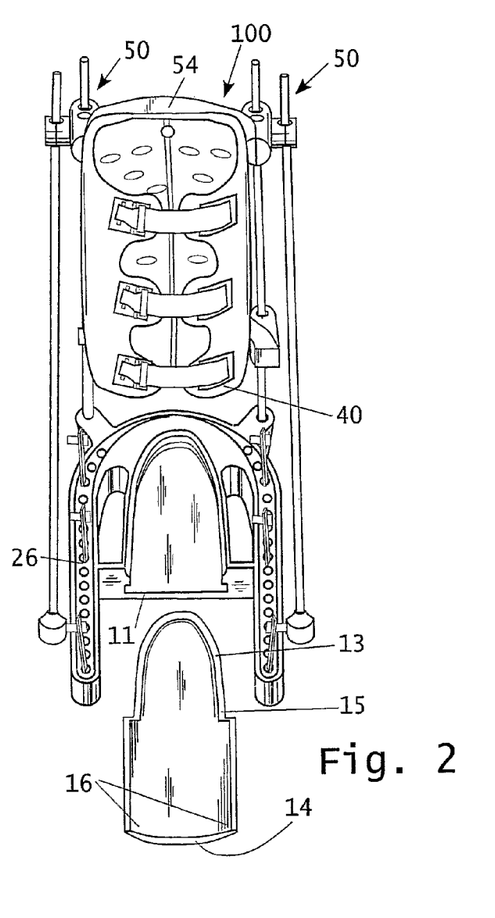
FIG. 2 is a top, front perspective view of the device of FIG. 1, with a removable plantar plate member removed.
Figures 3, 4:
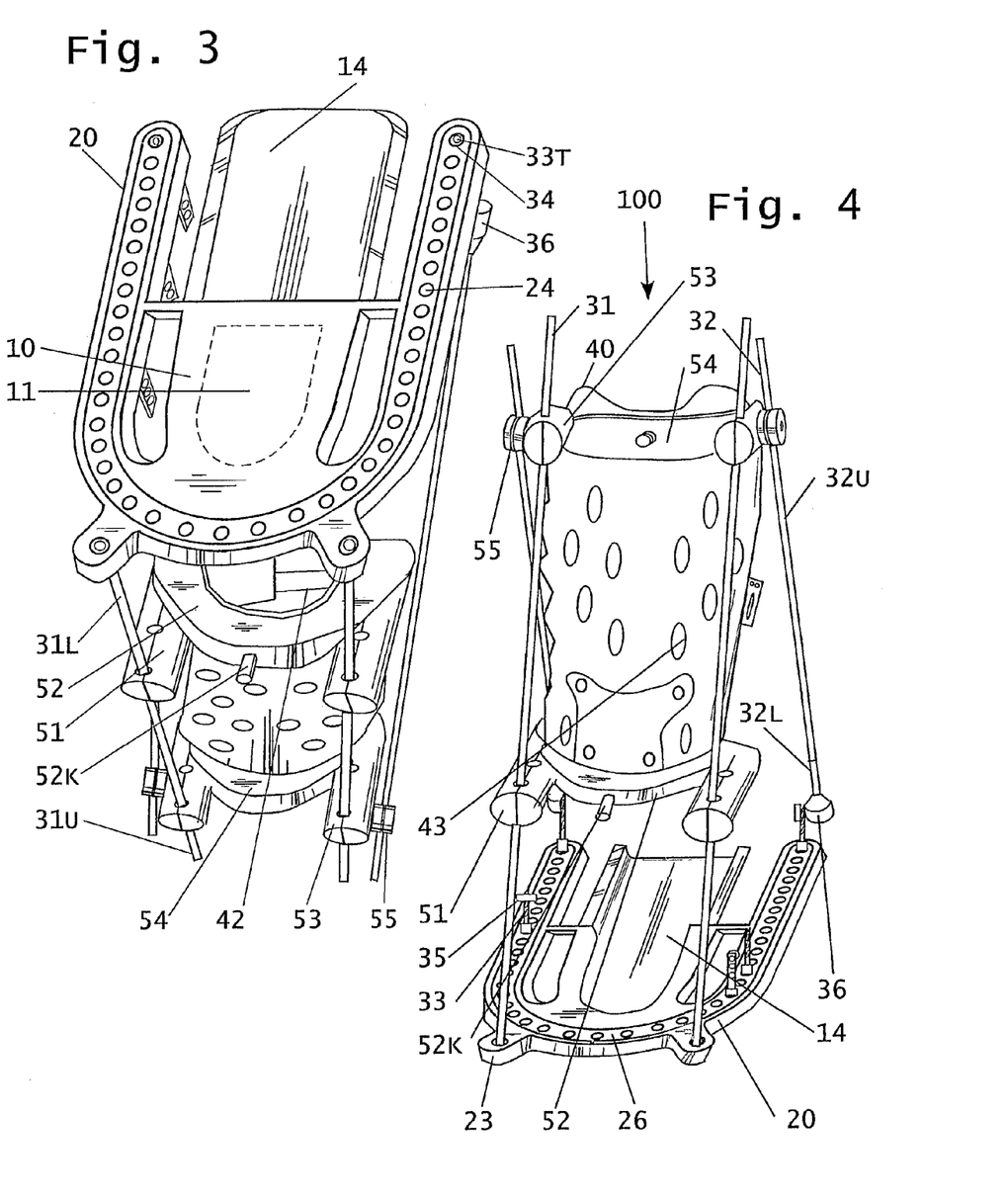
FIG. 3 is a bottom perspective view of the device of FIG. 1.
FIG. 4 is a rear perspective view of the device of FIG. 1.
Figure 5:
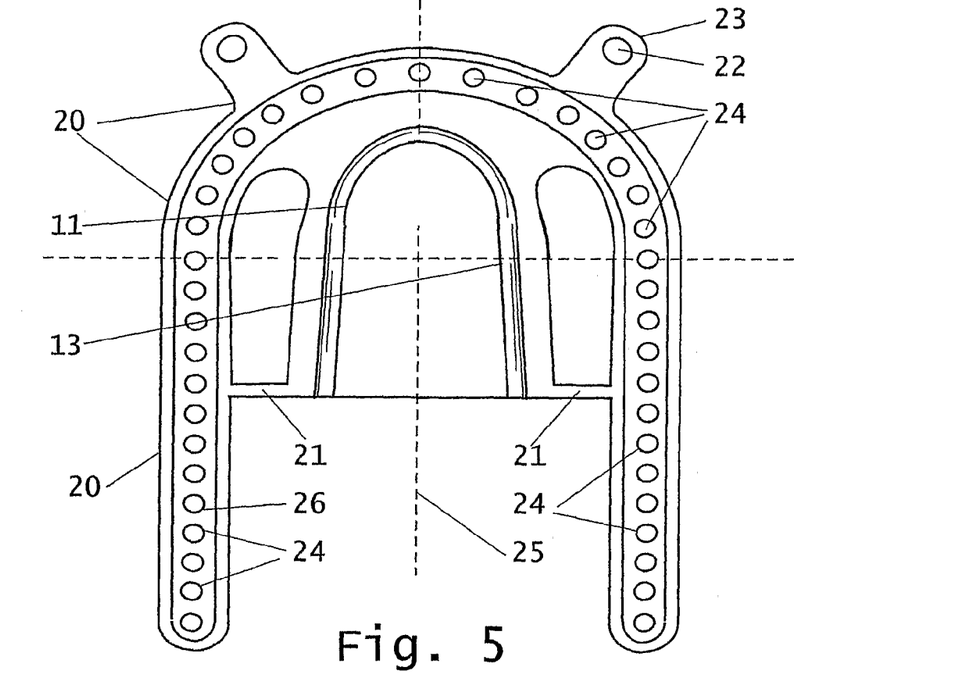
FIG. 5 is a top view of a plantar plate surrounded by a peripheral element, which has a removable plantar plate removed, found in the device of FIG. 1.
Figure 6:
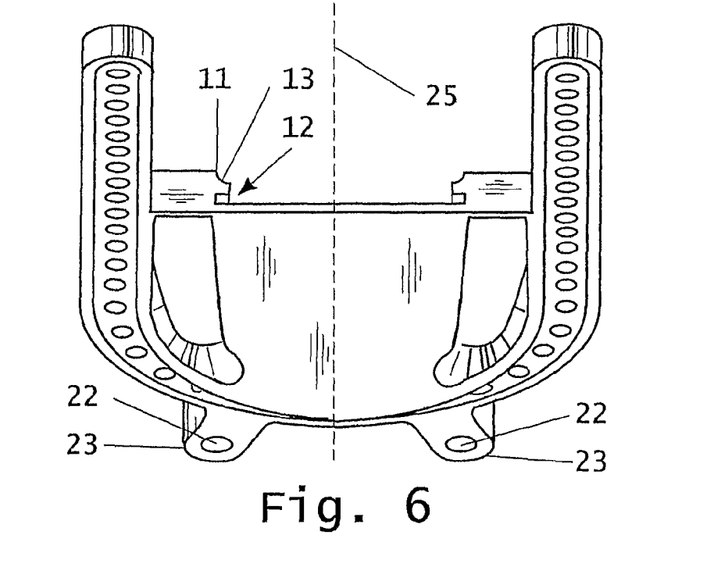
FIG. 6 is a bottom perspective view of the plate of FIG. 5.
Figure 7:
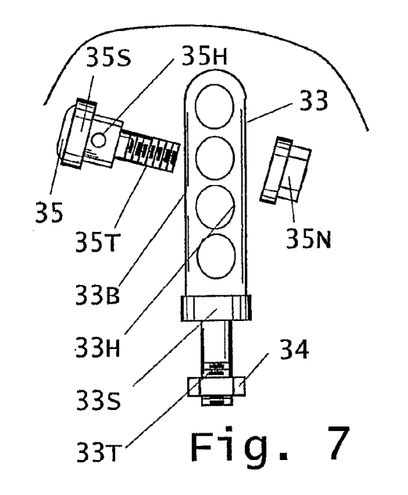
FIG. 7 is an exploded view of a perforate support post, which is shown with a surgical wire fastener ready for insertion into a hole of the fastener, and which can be attached to the peripheral element of the device of FIGS. 1 and 5.
Figure 8:
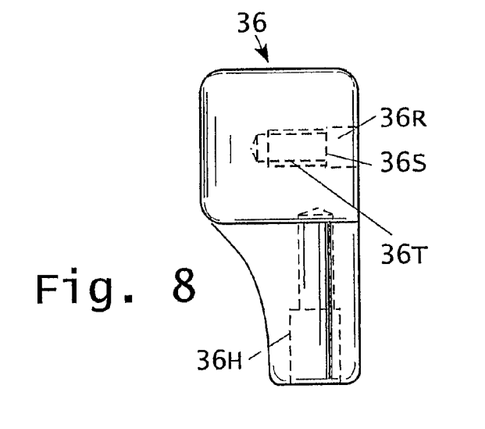
FIG. 8 is a side plan view of a lower pivotable fastener element of the device of FIG. 1.
Figure 9:
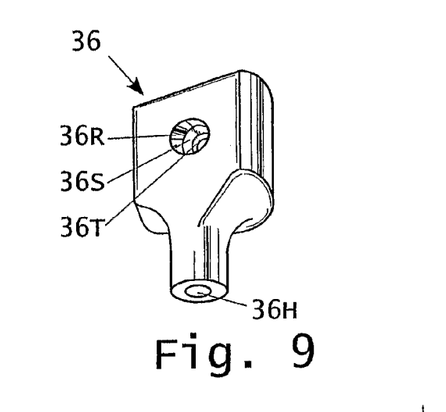
FIG. 9 is a perspective view of the element of FIG. 8.
Figure 10:
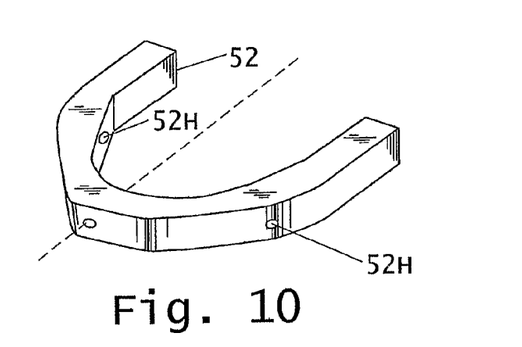
FIG. 10 is a rear perspective view of a lower, lower leg securing housing brace of the device of FIG. 1.
Figure 11:
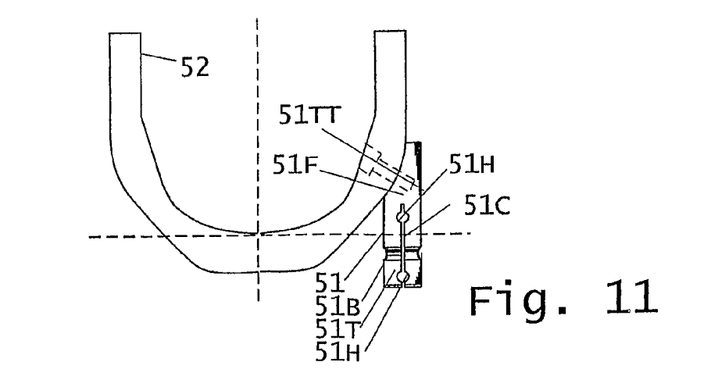
FIG. 11 is a top plan view of the brace of FIG. 10 to which is attached a vertically adjustable fastener, as found in the device of FIG. 1.
Figure 12:
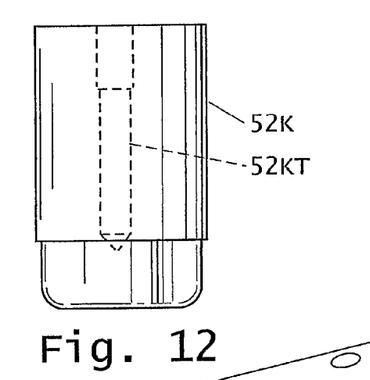
FIG. 12 is a plan view of a vertical adjusting handle of the device of FIG. 1.
Figure 13:
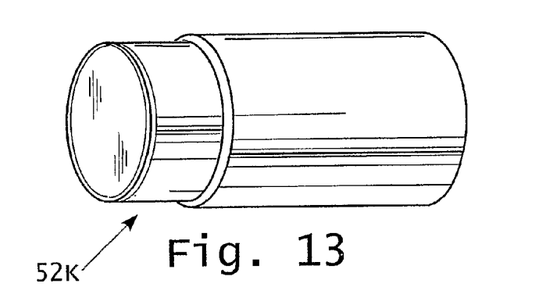
FIG. 13 is a perspective view of the handle of FIG. 12.
Figure 14:
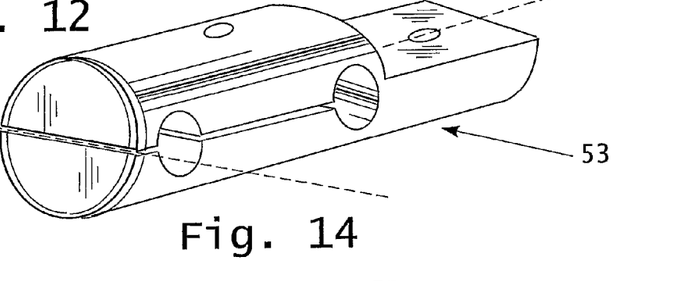
FIG. 14 is a perspective view of another vertically adjustable fastener configured for attachment to an upper, lower leg securing housing brace as found in the device of FIG. 1.
Figure 15:
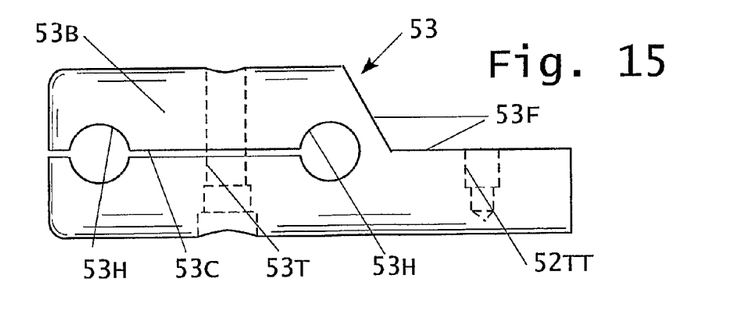
FIG. 15 is a top plan view of the fastener of FIG. 14.
Figure 16:
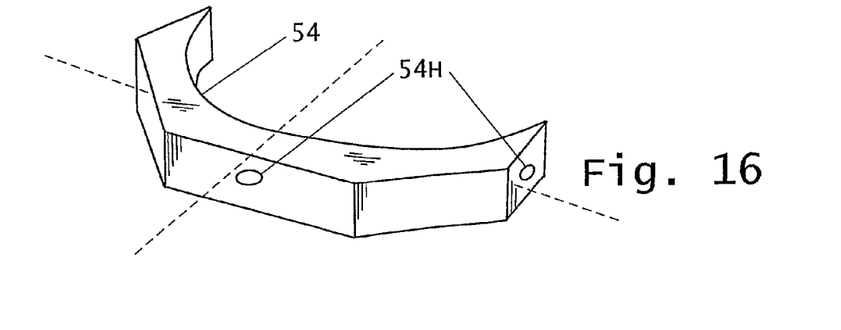
FIG. 16 is a rear perspective view of the upper, lower leg securing housing brace of the device of FIG. 1.
Figure 17:
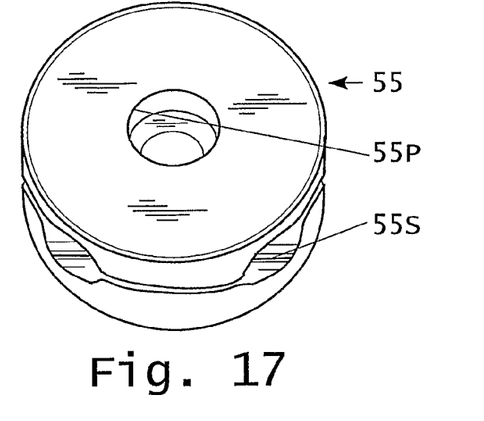
FIG. 17 is a perspective view of an upper pivotable fastener element found in the device of FIG. 1.
Figure 18:
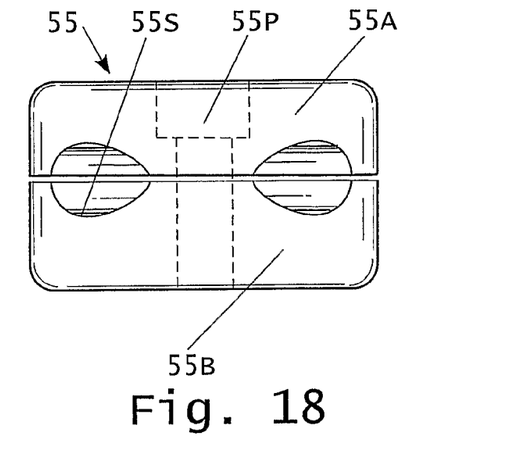
FIG. 18 is a plan view of the element of FIG. 17.
Figure 19:
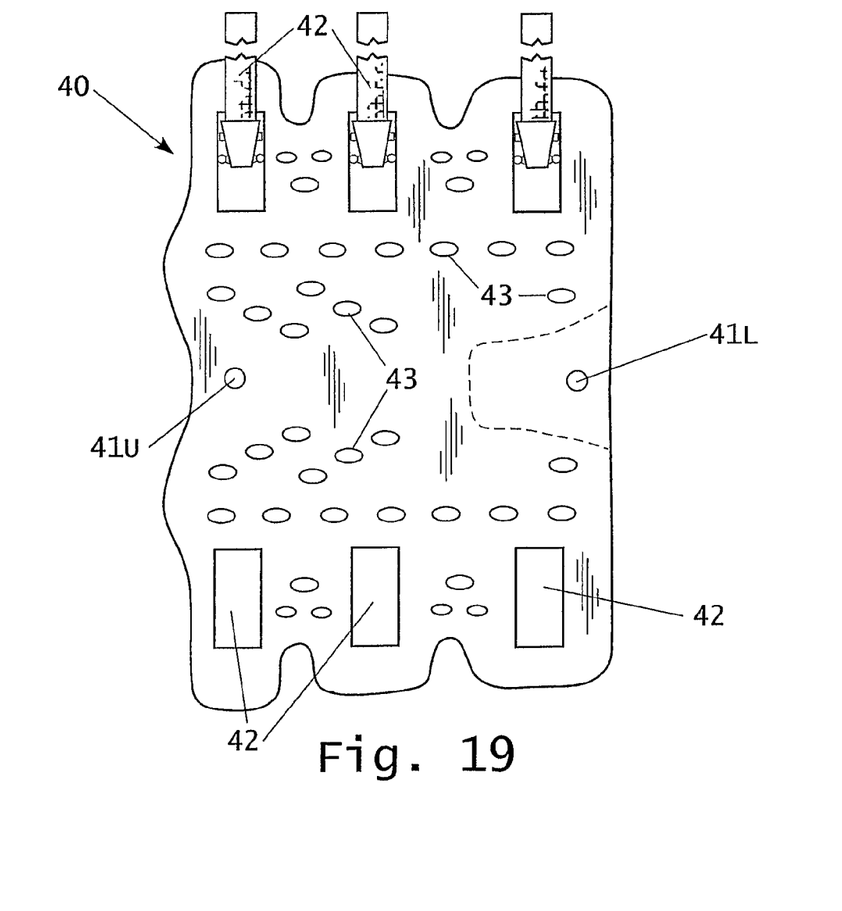
FIG. 19 is a plan view of a pattern for the lower leg securing housing of the device of FIG. 1.
Figure 20:
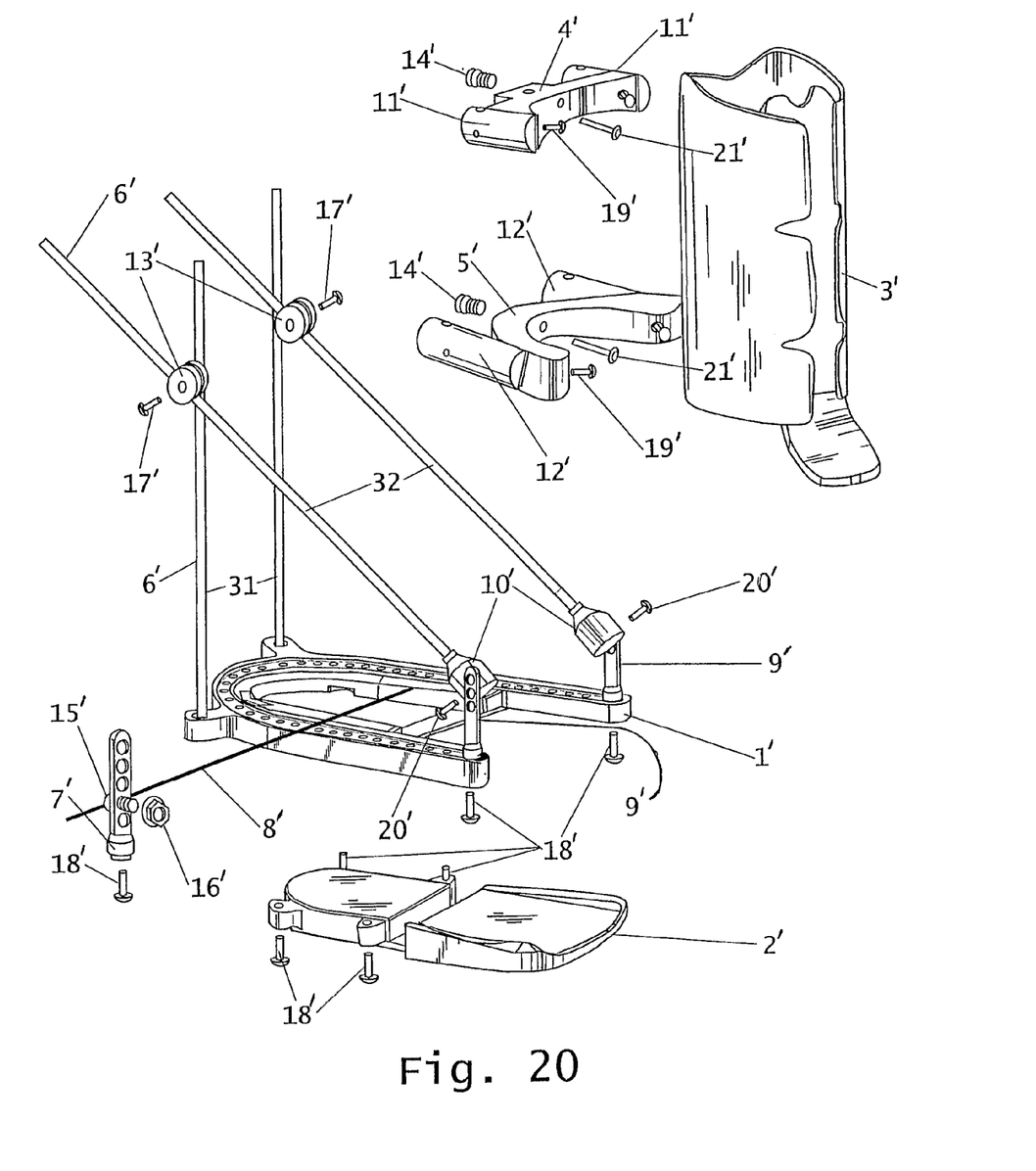
FIG. 20 is an exploded view of a further embodiment hereof.

| KEY TO FIG. 20 | | |
|---|---|---|
| Index Number | Part Name | Quantity |
| 1' (Compare 11-13) | Base ring, "GAROLITE" G10 layered glass fiber resin | 1 |
| 2' (Compare 14) | Foot plate, ABS plastic, machined or injection molded | 1 |
| 3' (Compare 40) | Support boot, upper portion of Darco Co. boot, cut | 1 |
| 4' (Compare 54) | Top bracket, ABS plastic, with embedded, threaded nut for 14'/21' | 1 |
| 5' (Compare 52) | Bottom bracket, ABS plastic, with embedded, threaded nut for 14'/21' | 1 |
| 6' (Compare 31, 32) | Rod, braided fiber carbon | 4 |
| 7' (Compare 33) | 5-Hole wire anchor, stainless steel | 1+ |
| 8' | K-wire, 16-inch (40.6-cm) standard | 1+ |
| 9' (Compare 33) | 3-Hole front wire anchor, stainless steel | 2 |
| 10' (Compare 36) | Front rod anchor, aluminum | 2 |
| 11' (Compare 53) | Top fixture, aluminum | 2 |
| 12' (Compare 51) | Bottom fixture, aluminum | 2 |
| 13' (Compare 55) | Frame disc, aluminum | 4 |
| 14' (Compare 52K) | Adjustment handle, aluminum | 2 |
| 15' (Compare 35) | Wire bolt, stainless steel | 1/anchor |
| 16' (Compare 35N) | Wire nut, stainless steel | 1/anchor |
| 17' | Button head screw, 1¼ inch (3.18-cm), stainless steel | 2 |
| 18' | Button head screw, 1-inch (2.54-cm), stainless steel | 7 |
| 19' | Button head screw, ¾-inch (1.9-cm), stainless steel | 4 |
| 20' | Button head screw, ½-inch (1.27-cm), stainless steel | 2 |
| 21' | Button head washer screw, 5/16-inch (0.8-cm), stainless steel | 2 |

-continued

KEY TO FIG. 20

| Index Number | Part Name | Quantity |
| --- | --- | --- |
| 31 | First, vertical support, as noted above and in FIGS. 1-4 | 2 |
| 32 | Second, horizontal support, as noted above and in FIGS. 1-4 | 2 |

The present invention is thus provided. Various feature(s), part(s), subcombination(s) and/or combination(s) can be employed with or without reference to other feature(s), part(s), subcombination(s) and/or combination(s) its practice, and numerous adaptations and modifications can be effected within its spirit, the literal claim scope of which is particularly pointed out as follows:

What is claimed is:

1. An adjustable restraint for the lower leg and/or foot comprising:
 a plantar plate surrounded by a peripheral element about which a plurality of supports can be positioned;
 a support system attachable to said plate or element, which can provide vertical and horizontal support in relation to said plate and element; and
 a lower leg securing housing;
wherein the lower leg securing housing is attachable to the support system through at least one adjustable fastener such that the lower leg securing housing can be adjusted vertically with respect to the plantar plate and secured in position therewith; and the support system includes:
 at least one first support attachable to said plate or element, which has a vertically extending component thereto, and which has upper and lower ends; and
 at least one second support laterally attachable to said plate or element disposed in relation to the at least one first support, which has a horizontally directed component thereto, which has upper and lower ends, and which is attachable about the lower end with a pivoting relationship to said plate or element;
wherein:
 the lower leg securing housing is attachable to the at least one first support through at least one first adjustable fastener; and
 the lower leg securing housing is attachable to the at least one second support through at least one second adjustable fastener.

2. The adjustable restraint of claim 1, wherein at least a sole portion of the plantar plate is made to be removable.

3. The adjustable restraint of claim 1, wherein said at least one first support and said at least one second support include thin, elongate rods.

4. The adjustable restraint of claim 2, wherein said at least one first support and said at least one second support include thin, elongate rods.

5. The adjustable restraint of claim 1, wherein each of said at least one first support and said at least one second support includes a pair of thin, elongate rods, a first of the pair on a left side of the adjustable restraint and a second of the pair on a right side of the adjustable restraint; and the leg securing housing is attached to:
 said at least one first support through the at least one first adjustable fastener and a lower brace that attaches to the leg securing housing across a lower rear portion of the leg securing housing; and
 said at least one second support through the at least one second adjustable fastener and an upper lower brace that attaches to the leg securing housing across an upper rear portion of the leg securing housing.

6. The adjustable restraint of claim 2, wherein each of said at least one first support and said at least one second support includes a pair of thin, elongate rods, a first of the pair on a left side of the adjustable restraint and a second of the pair on a right side of the adjustable restraint; and the leg securing housing is attached to:
 said at least one first support through the at least one first adjustable fastener and a lower brace that attaches to the leg securing housing across a lower rear portion of the leg securing housing; and
 said at least one second support through the at least one second adjustable fastener and an upper lower brace that attaches to the leg securing housing across an upper rear portion of the leg securing housing.

7. The adjustable restraint of claim 1, wherein among the plurality of supports that can be positioned about the peripheral element can be vertical post units that can secure a surgical wire in an Ilazarov procedure.

8. The adjustable restraint of claim 2, wherein among the plurality of supports that can be positioned about the peripheral element can be vertical post units that can secure a surgical wire in an Ilazarov procedure.

9. An adjustable restraint for the lower leg and/or foot comprising:
 a plantar plate surrounded by a peripheral element about which more than two supports can be positioned, among which supports can be vertical post units that can secure a surgical wire in an Ilazarov procedure;
 a support system attachable to said plate or element, which can provide vertical and horizontal support in relation to said plate and element; and
 a lower leg securing housing;
wherein the lower leg securing housing is attachable to the support system through at least one adjustable fastener such that the lower leg securing housing can be adjusted vertically with respect to the plantar plate and secured in position therewith.

10. The adjustable restraint of claim 9, wherein the peripheral element includes at least one receptacle set such that the support system plus said vertical post units can be positioned therewith.

11. The adjustable restraint of claim 10, wherein the at least one receptacle set includes a first receptacle set in a posterior position and a second receptacle set in a horseshoe shaped configuration on opposing side and posterior positions.

12. The adjustable restraint of claim 11, wherein the support system further includes:
 at least one first support attachable to said plate or element, which has a vertically extending component thereto, and which has upper and lower ends; and
 at least one second support laterally attachable to said plate or element disposed in relation to the at least one first support, which has a horizontally directed component thereto, which has upper and lower ends, and which is attachable about the lower end with a pivoting relationship to said plate or element;

wherein:
the lower leg securing housing is attachable to the at least one first support through at least one first adjustable fastener; and
the lower leg securing housing is attachable to the at least one second support through at least one second adjustable fastener; and
wherein each of said least one first support and said at least one second support includes a pair of thin, elongate rods, a first of the pair on a left side of the adjustable restraint and a second of the pair on a right side of the adjustable restraint; and the leg securing housing is attached to:
said at least one first support through the at least one first adjustable fastener and a lower brace that attaches to the leg securing housing across a lower rear portion of the leg securing housing; and
said at least one second support through the at least one second adjustable fastener and an upper lower brace that attaches to the leg securing housing across an upper rear portion of the leg securing housing.

13. The adjustable restraint of claim 9, wherein at least a sole portion of the plantar plate is removable.

14. The adjustable restraint of claim 10, wherein at least a sole portion of the plantar plate is removable.

15. The adjustable restraint of claim 11, wherein at least a sole portion of the plantar plate is removable.

16. The adjustable restraint of claim 12, wherein at least a sole portion of the plantar plate is removable.

17. An adjustable restraint for the lower leg and/or foot comprising:
a plantar plate enclosed on three sides by a peripheral element about which a plurality of supports can be positioned;
a support system attachable to said plate or element, which can provide vertical and horizontal support in relation to said plate and element; and
a lower leg securing housing;
wherein the lower leg securing housing is attachable to the support system through at least one adjustable fastener such that the lower leg securing housing can be adjusted vertically with respect to the plantar plate and secured in position therewith.

18. The adjustable restraint of claim 17, wherein at least a sole portion of the plantar plate is made to be removable.

19. An adjustable restraint for the lower leg and/or foot comprising:
a plantar plate surrounded by a peripheral element about which a plurality of supports can be positioned;
a support system attachable to said plate or element, which can provide vertical and horizontal support in relation to said plate and element; and
a lower leg securing housing;
wherein the lower leg securing housing is attachable to the support system through at least one adjustable fastener such that the lower leg securing housing can be adjusted vertically with respect to the plantar plate and secured in position therewith; and the peripheral element includes at least one receptacle set such that the support system plus vertical post units that can secure a surgical wire in an Ilazarov procedure can be positioned therewith.

20. The adjustable restraint of claim 19, wherein at least a sole portion of the plantar plate is made to be removable.

* * * * *